United States Patent [19]

Roblejo

[11] Patent Number: 4,526,575

[45] Date of Patent: Jul. 2, 1985

[54] HYDROPROPULSION CATHETER AND METHOD FOR REMOVING URINARY BLOCKAGES

[76] Inventor: Conrad Roblejo, 23 Acorn Hill Dr., Voorhees, N.J.

[21] Appl. No.: 428,877

[22] Filed: Sep. 30, 1982

[51] Int. Cl.[3] .......... A61M 5/00

[52] U.S. Cl. .......... 604/54; 128/66; 128/328; 604/150

[58] Field of Search .......... 604/20, 22, 54, 28-30, 604/150; 128/66, 328

[56] References Cited

U.S. PATENT DOCUMENTS

| | | | |
|---|---|---|---|
| 1,819,368 | 8/1931 | Hart | 604/27 X |
| 1,846,596 | 2/1932 | Hertzberg | 604/30 X |
| 3,874,372 | 4/1975 | Le Bon | 128/66 X |
| 3,883,074 | 5/1975 | Lambert | 128/66 X |
| 3,993,054 | 11/1976 | Newmann | 128/66 |
| 4,305,395 | 12/1981 | Martinez | 604/28 |
| 4,365,752 | 12/1982 | Waisbren et al. | 128/66 X |

*Primary Examiner*—Dalton L. Truluck

[57] ABSTRACT

A device for removing urinary blockages in small male animals comprising non-traumatic needle adapted to be inserted in the urethra of the animal, connected to means for introducing a pulsating liquid flow through said needle is disclosed. Also disclosed is a method of removing urinary blockages in small male animals comprising inserting said needle in the urethra.

8 Claims, 2 Drawing Figures

HYDROPROPULSION CATHETER AND METHOD FOR REMOVING URINARY BLOCKAGES

BACKGROUND OF THE INVENTION

1. Field of the Invention

This invention relates to a medical device and method for removing urinary blockages.

2. Description of the Prior Art

The generally accepted, conventional method for removing urinary blockages in small male animals is to use a "Tom Cat" catheter which is attached to a syringe. The doctor inserts the catheter and squeezes the syringe to introduce liquid pressure to break up the blockage. Frequently this method takes an extended period of time, sometimes a half hour up to two hours, and is very painful for the animal, and in some instances is traumatic due to heat generation during lengthy procedures, especially with the cavitran method. When the "Tom Cat" method takes too long, the doctor then resorts to shaving the abdomen and performing a bladder tapping operation called cystocentesis.

SUMMARY OF THE INVENTION

It is an object of the present invention to provide a new medical device to permit very rapid and relatively painless method of removal of urinary blockages.

Another object is to provide a method of removing urinary blockages, especially in small animals such as cats, which is quick, efficient, and non-traumatic.

These objects and others as will become apparent from the following disclosure, are achieved by the present invention which comprises a device for removing urinary blockages in small animals comprising a non-traumatic needle adapted to be inserted in the urethra of the animal and connected to means for introducing a pulsating liquid flow through said needle. Another aspect of the invention is the method of removing the blockages using the device.

DETAILED DESCRIPTION OF THE INVENTION AND PREFERRED EMBODIMENTS

Figure 1:
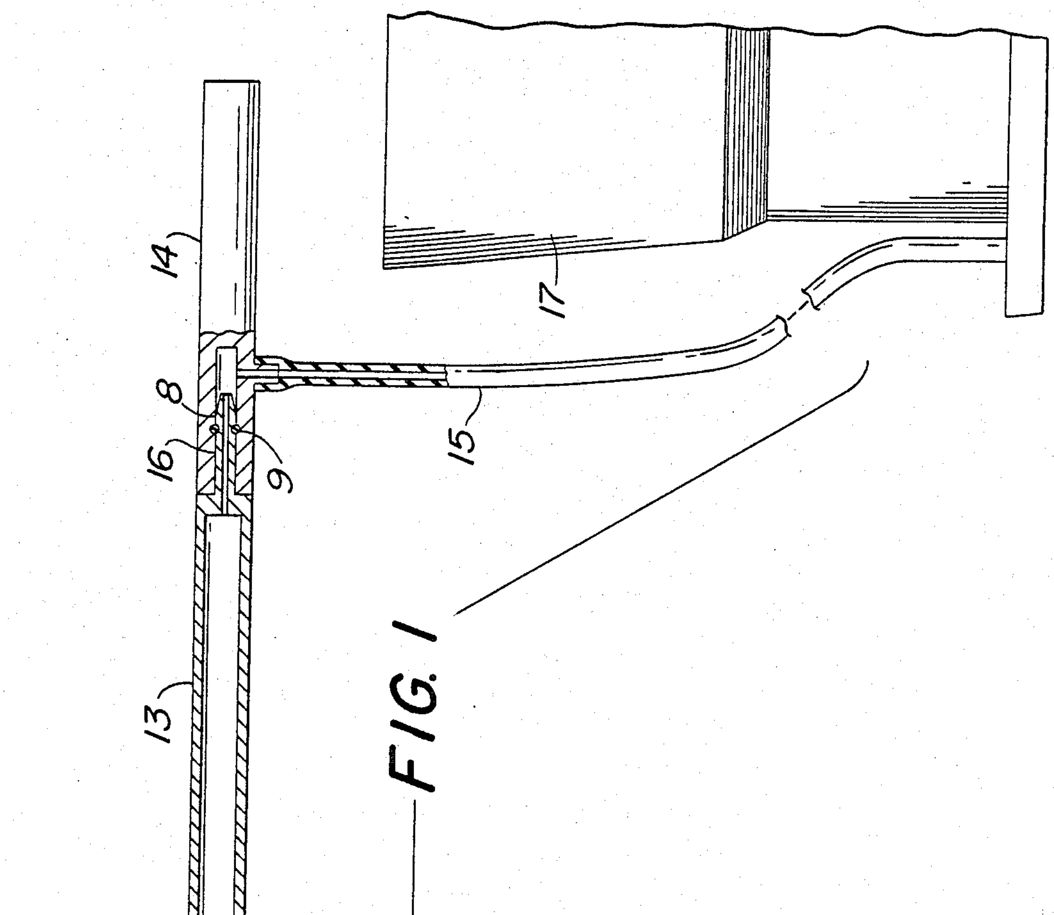
FIG. 1 is a cross-sectional side view of a handle and atraumatic needle and a schematic elevational view of the means for generating pulsating liquid flow.
Figure 1:
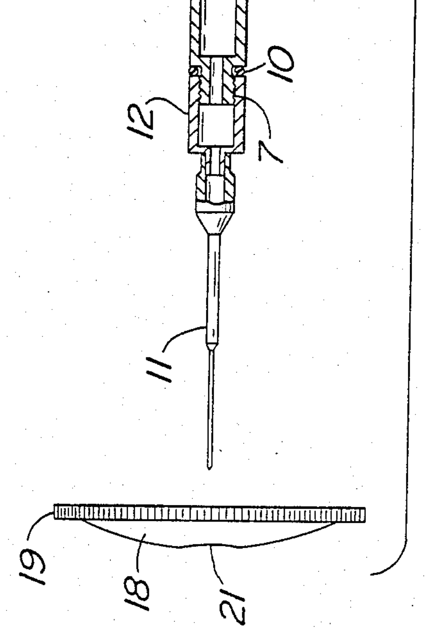

In FIG. 1 there is shown a device for removing urinary blockages in accordance with the invention wherein a non-traumatic needle 11 fits onto a stainless steel adapter 12 which is threaded so as to fit the threads 7 of the stainless steel handle 13. The adapter 12 and handle 13 are sterilizable, and are normally sterilized between operative procedures. The handle 13 has a tapered end 16 with a shoulder 8 adapted to fit the "Water-pik" plastic sleeve 14, which in turn is connected by plastic pipe 15 to a "Water-pik" pulsating pump 17. An O-ring 9 aids in retention of tapered end 16 in sleeve 14.

The "Water-pik" element of the device is preferably the conventional type typically used for cleaning teeth by a pulsating jet of water; except the conventional plastic jet is not inserted into sleeve 14, but is replaced by handle 13, and instead of water, a saline solution is typically used. Preferably the solution used is 0.9% saline, and contains a small amount of antibiotic. The device of the invention can also be used to clean tear and salivary ducts, and anal sacs which sometimes become abcessed. In such an application, the saline solution can be replaced by antibiotic-containing solution.

While any needle can be used, the preferred type is a lacrimal canula or #20-25 guage, preferably #23 gauge when the device is to be used on a cat, blunt tip or non-traumatic tip metal needle. A plastic "Tom Cat" catheter can also be attached to the adapter as an alternative to the metal needle, in cases where the blockage is especially far back.

The handle 13 or "hydrocatheter," is preferably pencil shaped for ease of handling and use.

Figure 2:
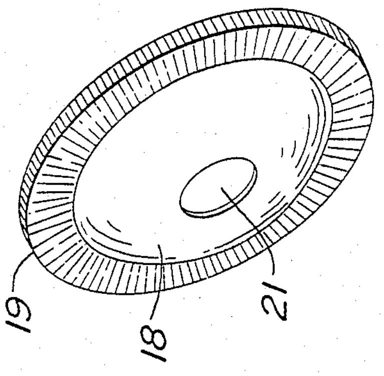
FIG. 2 is a front schematic view of a disc in accordance with the invention.

In some small animals, for example cats, a convex plastic disc 19 in FIGS. 1 and 2 having hole 21 and convex area 18 is used by pressing it against the animal's body to cause protrusion of the penis prior to insertion of the needle.

The "Water-pik" hydraulic oscillator produces a pulsed output from a steady flow input. Other means for generating and introducing a pulsating liquid flow through the handle and needle can be used.

In use the purpose of the device is to catheterize male animals which are unable to micturate because of urethral blockage. The patient is usually sedated and anesthetized, and placed on lateral recumbency. About 75 ml. of warm saline solution can be introduced to the "Water-pik" reservoir, along with 2 ml. of Kanamycin sulfate solution. Then the disc is used to cause protrusion of the penis. With the penis being held in one hand, and the needle being inserted with the other hand, the pulsation of the water is turned on, and a gentle forward and backward motion of the catheter is used. Immediately, portions of crystal can be observed being removed from the urethra and within a few seconds the entire blockage is removed, rather than the much longer period required using the prior devices.

While this invention has been described in great detail, it is to be understood that various modifications, alternatives, and improvements can be made without departing from the spirit and scope of the present invention as defined by the following claims.

I claim:

1. Device for removing urinary blockages in small male animals comprising non-traumatic needle adapted to be inserted in the urethra of the animal, means for positioning the needle into the penis of the small animal, and means for introducing a pulsating liquid flow through said needle.

2. Device in accordance with claim 1 wherein said means is a hydraulic oscillator.

3. Device in accordance with claim 1 wherein said needle is a number 20 to 25 gauge lacrimal canula.

4. Device in accordance with claim 1 wherein said needle is a flexible plastic catheter.

5. Device in accordance with claim 1 wherein said means for positioning is a convex plastic disc adapted to the size of the animal's penis.

6. Method of removing urinary blockages in small male animals comprising inserting an non-traumatic needle in the urethra of the animal, and then introducing pulsating liquid through the needle, thereby immediately dislodging the blockage.

7. Method in accordance with claim 6 wherein the liquid introduced through the needle is a warm saline solution.

8. Method in accordance with claim 6 wherein the penis is inserted through a hole in the center of a convex plastic disc adapted to the size of the animal's penis and the disc is pressed against the animal's body to cause protrusion of the penis prior to insertion of the needle.

* * * * *